United States Patent [19]

Davey

[11] Patent Number: 5,318,587
[45] Date of Patent: Jun. 7, 1994

[54] PLEATED BALLOON DILATATION CATHETER AND METHOD OF USE

[75] Inventor: Christopher T. Davey, Lawrence, Mass.

[73] Assignee: C. R. Bard, Inc., Murray Hill, N.J.

[21] Appl. No.: 956,454

[22] Filed: Oct. 2, 1992

Related U.S. Application Data

[63] Continuation of Ser. No. 759,741, Sep. 12, 1991, abandoned, which is a continuation of Ser. No. 398,630, Aug. 25, 1989, abandoned.

[51] Int. Cl.⁵ ............................................. A61M 29/02
[52] U.S. Cl. ...................................... 606/194; 604/96
[58] Field of Search ............... 606/194, 192, 193, 196, 606/195; 604/96-103

[56] References Cited

U.S. PATENT DOCUMENTS

| | | | |
|---|---|---|---|
| Re. 30,365 | 8/1980 | Mattler | 128/349 B |
| 797,676 | 8/1905 | Flowers | 604/96 |
| 2,442,573 | 6/1948 | Stafford | 128/242 |
| 2,687,719 | 8/1954 | Hoyt | 606/192 X |
| 3,459,175 | 8/1969 | Miller | 128/2 |
| 3,472,230 | 10/1969 | Fogarty | 128/328 |
| 3,896,816 | 7/1975 | Mattler | 128/349 B |
| 3,916,906 | 11/1975 | Gerry | 606/192 |
| 4,141,364 | 2/1979 | Schultze | 606/192 X |
| 4,178,739 | 12/1979 | Stephens | 604/99 X |
| 4,195,637 | 4/1980 | Gruntzig et al. | 604/97 X |
| 4,276,874 | 7/1981 | Wolvek et al. | 128/1 D |
| 4,335,168 | 6/1982 | Ergaver | 428/36.9 |
| 4,459,977 | 7/1984 | Pizon et al. | 606/194 X |
| 4,490,421 | 12/1984 | Levy | 604/96 X |
| 4,608,984 | 9/1986 | Fogarty | 128/344 |
| 4,644,936 | 2/1987 | Schiff | 128/1 D |
| 4,790,831 | 12/1988 | Skribiski | 604/282 |
| 4,941,877 | 7/1990 | Montano | 604/96 |
| 4,950,232 | 8/1990 | Ruzicka | 604/96 |
| 5,015,231 | 5/1991 | Keith et al. | 604/96 |
| 5,087,246 | 2/1992 | Smith | 604/103 X |

FOREIGN PATENT DOCUMENTS

| | | | |
|---|---|---|---|
| 0376451 | 7/1990 | European Pat. Off. | |
| 716289 | 12/1931 | France | 604/97 |
| 1327858 | 8/1973 | United Kingdom | 604/96 |

*Primary Examiner*—Michael H. Thaler
*Attorney, Agent, or Firm*—Wolf, Greenfield & Sacks

[57] ABSTRACT

A balloon dilatation catheter is provided with a pleated balloon defining at least three pleats and alternating wings. When the balloon collapses, it tends to assume a pleated configuration which defines a lower profile and is better adapted to pass through narrow channels, such as a guide catheter. The balloon is formed from a polymeric material in a method that involves the steps of extruding a tube having at least three circumferentially spaced, longitudinally extending segments of less wall thickness than the remainder of the tube, and biaxially stretching the tube to a predefined shape while maintaining the longitudinal segments of reduced wall thickness.

10 Claims, 1 Drawing Sheet

U.S. Patent    June 7, 1994    5,318,587
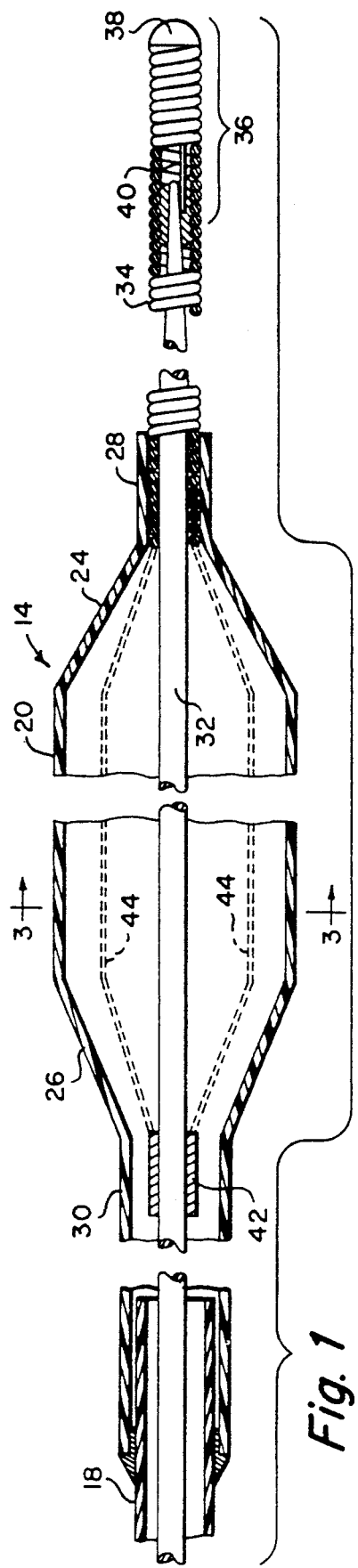
Fig. 1
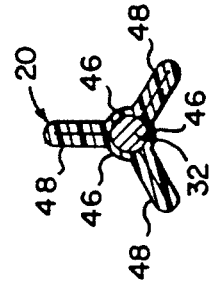
Fig. 4
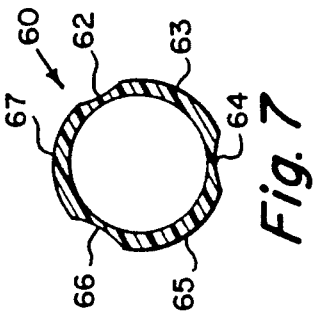
Fig. 7
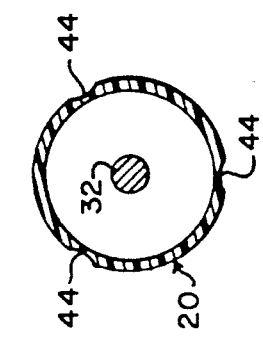
Fig. 3
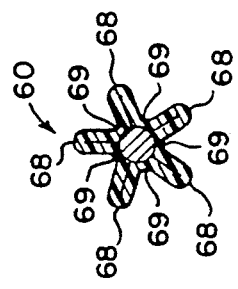
Fig. 6
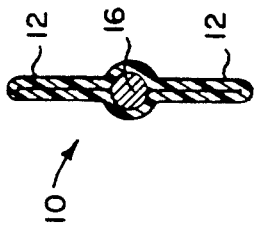
Fig. 2 (PRIOR ART)
Fig. 5

PLEATED BALLOON DILATATION CATHETER AND METHOD OF USE

This application is a continuation of application Ser. No. 07/759,741, filed Sep. 12, 1991, now abandoned, which is a continuation of application Ser. No. 07/398,630, filed Aug. 25, 1989, now abandoned.

FIELD OF THE INVENTION

This invention relates to balloon catheters used for dilatation procedures.

BACKGROUND OF THE INVENTION

Balloon dilatation catheters are used for a variety of medical procedures, including dilation of obstructed body lumens, such as blood vessels, coronary arteries and the esophageal tract. In particular, such catheters are used in angioplasty procedures to enlarge the lumen of a blood vessel which is constricted or stenosed by arteriosclerosis.

In a type of angioplasty known as percutaneous transluminal coronary angioplasty (PTCA), dilatation catheters are used in conjunction with a guide catheter through which the dilatation catheter is inserted and guided to the desired location in the body lumen. In a typical PTCA procedure, the guide catheter is percutaneously introduced into the patient's arterial system and is fluoroscopically guided to the entrance to the coronary artery. A dilatation catheter, having a balloon at its distal end, then is passed through the guide catheter, so that the balloon extends beyond the distal end of the guide catheter into the coronary artery. The catheter then is manipulated to place the balloon (deflated) into the obstruction. Once the balloon is placed within the obstruction, it is inflated to dilate the obstructed lumen.

The balloon of the dilatation catheter must be deflated to a low profile in order for it to be passed through the guide catheter and, more particularly, through the stenosis. The balloon is deflated by applying negative pressure to the balloon through an inflation/deflation lumen that extends from the proximal end of the catheter to the interior of the balloon. The configuration assumed by the balloon upon deflation presents a problem in catheter utilization. Typically, the balloon forms a pair of opposed, radially-extending, flat wings, when collapsed under the influence of negative pressure, as shown in FIG. 2. To insert the balloon into the lumen of a guide catheter, the physician must manually wrap the wings about the catheter shaft prior to insertion into the guide catheter. The reduced profile of the balloon, caused by the wrapping, facilitates insertion of the balloon into the guide catheter and the obstruction. However, after the balloon has been inflated in the patient and it is desired to recollapse the balloon, the balloon will again tend to assume the two wing configuration. The radial extent of the opposed wings may make it difficult for the balloon to refold as it is withdrawn into the guide catheter or if it is desired to recollapse the balloon and advance it to another stenosed location. In the latter case, the radial extending wings may make it more difficult for the balloon to be inserted into the stenosis.

A desirable feature of a balloon dilatation catheter, therefore, is a balloon which has a reduced profile to facilitate insertion into a guide catheter and a vascular stenosis, without the need to manually wrap the balloon about the catheter shaft.

The foregoing problem has not gone unrecognized as evidenced by proposed devices to provide a means for causing a dilatation balloon to be wrapped closely about a catheter shaft to form a reduced profile. For example, see U.S. Pat. No. 4,292,974, issued to Fogerty. Notwithstanding such proposals, there remains a need for a simple effective means to facilitate collapse of a dilatation balloon to a low profile.

A further problem encountered in using dilatation balloon catheters is the failure of the balloon to deflate, following dilatation of the obstruction. Because of a malfunction in the catheter itself, the dilatation balloon may fail to deflate when aspirated. In these instances, the balloon must be intentionally destroyed before withdrawal through the guide catheter. The balloon is destroyed by inflating the balloon to a pressure at which the balloon wall ruptures or bursts. Unfortunately, many current dilatation balloons have burst pressures which exceed the delivery capabilities of most clinical inflation devices, often requiring burst pressures in excess of 20 Bars. Such pressure may rupture the body lumen as well as the dilatation balloon, thereby creating an undesirable hazard to the patient. A further desirable feature of a dilatation catheter, therefore, is to provide a balloon having an artificially lower burst pressure to facilitate easy destruction of the balloon, if necessary.

SUMMARY OF THE INVENTION

In accordance with the invention, a balloon for a dilatation catheter has at least three longitudinally extending segments of reduced wall thickness. In particular, the segments form fold lines, extending longitudinally of the balloon and causing the balloon to collapse into a pleated configuration when aspirated. When inflated, the pleats expand so that the balloon forms the cylindrical configuration desired for dilatation. The pleated balloon of the present invention defines wings having shorter radial dimensions. The wings are more easily collapsed. They define a reduced profile when collapsed to facilitate insertion and withdrawal through a guide catheter as well as a stenosis. The present invention further provides a dilatation catheter having the balloon described above, as well as a tubular extrusion from which the balloon may be made.

Another object of the invention relates to a method for forming a pleated balloon. A tubular extrusion of a polymeric material is formed having a plurality of circumferentially spaced, longitudinally extending lines defined by less wall thickness than the remainder of the tube. The balloon is formed by biaxially stretching the tubular extrusion, in accordance with the method described in U.S. Pat. No. 4,490,421, issued to Levy.

It is among the general objects of the invention to provide a balloon configuration for a dilatation catheter which incorporates an improved means for collapsing the balloon to a low profile.

Yet another object of the present invention is to provide a catheter having a dilatation balloon which collapses in a manner that defines at least three pleats and alternating wings.

A further object of the present invention is to provide a method for forming a pleated balloon.

Yet another object of the present invention is to provide a dilatation catheter having a balloon which, when withdrawn through the lumen of a guide catheter, will reduce the risk of damage to the balloon wall.

A further object of the present invention is to provide a dilatation catheter having a balloon with a predetermined burst pressure.

Still another object of the invention is to provide a dilatation balloon which, when the balloon bursts, does so along the length of the balloon.

DESCRIPTION OF THE DRAWINGS

The foregoing and other objects and advantages of the invention will be appreciated more fully from the following further description thereof, with reference to the accompanying drawings wherein:

FIG. 1 is an enlarged longitudinal sectional illustration of the distal end of a dilatation catheter of the present invention;

FIG. 2 is a cross-sectional illustration through a dilatation balloon showing the manner in which typical prior art dilatation balloons collapse to form a pair of diametrically opposed wings;

FIG. 3 is a sectional illustration of the dilatation catheter balloon of FIG. 1 as seen along lines 3—3 of FIG. 1;

FIG. 4 is a sectional illustration of the balloon of FIG. 3 in which three pleats are formed when in an evacuated, collapsed configuration;

FIG. 5 is a sectional illustration of an alternate embodiment of the balloon of FIG. 3 in which four pleats are formed when in an evacuated, collapsed configuration;

FIG. 6 is a sectional illustration of an alternate embodiment of the balloon of FIG. 3 in which five pleats are formed when in an evacuated, collapsed configuration; and FIG. 7 is a cross-sectional illustration of a tubular extrusion used in the method of manufacturing the pleated balloon of the present invention.

DETAILED DESCRIPTION OF THE PREFERRED EMBODIMENT

FIG. 2 illustrates, diagrammatically, the cross-sectional configuration assumed by a typical dilatation balloon 10 when the balloon is aspirated by applying negative pressure to the balloon interior, causing it to deflate. Balloon 10 forms a pair of diametrically opposed wings 12 as the balloon collapses. The physician typically must manually wrap the wings 12 about the catheter shaft 16, creating a low profile configuration which permits easy insertion of the dilatation catheter into the lumen of a guide catheter. Difficulty may arise, following the dilation procedure, either when it is desired to withdraw the dilatation catheter through the lumen of the guide catheter or when it is desired to deflate the balloon and reposition it at another vascular location to perform another dilatation. In particular, the diametrically opposed wings 12 may not wrap closely about the catheter shaft as the catheter is withdrawn back into the guide catheter or is repositioned within the arteries. Instead, the wings may catch on the distal opening of the guide catheter or may preclude reinsertion of the balloon into another stenosis.

In accordance with the present invention, a deflated dilatation balloon has a low profile configuration having at least three pleats and alternating wings. When such a balloon is collapsed, each of the wings is relatively short, in its radial extent, and collapses more readily about the catheter shaft. When inflated, the balloon assumes a cylindrical configuration.

In accordance with one embodiment of the present invention, as shown in FIGS. 1 and 3, a dilatation catheter 14 includes an elongate flexible shaft 18 having a dilatation balloon 20 carried at the distal end of the shaft. An inflation lumen 22 extends through shaft 18 from the proximal to the distal end and is in fluid communication with the interior of balloon 20. The proximal end of the shaft (not shown) is adapted to be connected to a suitable fitting, such as a luer fitting, by which an inflation/deflation device such as a syringe may be connected. Shaft 18 may be formed from an appropriate polymeric material as will be appreciated by those familiar with the art. Dilatation balloon 20 includes an elongate cylindrical portion having a pair of tapered conical sections 24 and 26 at its distal and proximal ends, respectively. A distal collar 28 and a proximal collar or an elongate sleeve 30 extend from conical ends 24 and 26, respectively. The dilatation balloon may be formed from a polymeric material such as polyethylene terephthalate and may be formed in accordance with the method of the present invention, as described hereinafter.

Proximal sleeve 30 is adhesively attached to the distal end of shaft 18 as shown in FIG. 1. A support wire 32 extends through lumen 22, the interior of balloon 20, and distally therebeyond. The annual space surrounding support wire 32 provides an annular inflation/deflation lumen in fluid communication with the interior of balloon 20. The support wire 32 has a tapered distal tip which extends into and is attached to a helically-wound radiopaque coil 34. Coil 34 has a distal tip 36 terminating with a rounded weld bead 38. The distal collar 28 of balloon 20 is adhesively attached to the proximal end of coil 34, as shown in FIG. 1. The distal tip 36 of coil 34 may include a bendable, stainless steel shaping ribbon 40, which is secured to the distal tip of support wire 32 at one end and to weld bead 38 at the other end.

Catheter 14 may include a radiopaque marker band 42, securely attached to support wire 34, near the proximal portion of balloon 20. The marker band provides a means by which the physician can fluoroscopically verify the position of balloon 20.

FIG. 3 is a sectional illustration of the dilatation balloon 20 as seen along lines 3—3 of FIG. 1. By way of example, in a catheter adapted for coronary arterial use, the balloon of the dilatation catheter illustrated may have an inflated diameter of between 1.5 mm to 4.0 mm. The cylindrical midportion of balloon 20 may be 2 cm long. The end cones 24 and 28 may be about 4 to about 7 mm long. It should be understood, however, that the invention contemplates use in dilatation balloons other than for coronary angioplasty use and that the dimensions of such other balloons may vary from those illustrated and described herein.

The wall of balloon 20 is relatively thin. By way of example, for a balloon having an inflated diameter of 3.0 mm, an appropriate wall thickness would be between about 0.00025" to about 0.00050". The cones 24, 26 and collars 28, 30 may be thicker because they are expanded to a lesser degree than the cylindrical midportion of the balloon during the balloon fabrication process, discussed below.

As shown in FIG. 3, balloon 20 has a plurality of circumferentially spaced lines 44 of reduced wall thickness. Lines 44 extend longitudinally of balloon 20, as shown in phantom in FIG. 1. For a dilatation balloon of about 3.0 mm diameter having a wall thickness from between 0.00025" to 0.00050", the wall thickness at lines 44 may be approximately 0.00025". Lines 44 extend longitudinally of balloon 20 from distal collar 28 to proximal sleeve 30.

When balloon 20 is deflated by aspirating inflation lumen 22, the balloon collapses more easily along the lines 44 to create a substantially reduced profile characterized by three pleats 46 disposed intermediate three wings 48. It will be appreciated that the radial extension of each of the wings 48 of balloon 20 is considerably less than the radial extension of wings 12 in the unpleated balloon of FIG. 2.

The reduced profile assumed by balloon 20 upon evacuation not only minimizes the necessity for the balloon to be wrapped prior to insertion into the guide catheter, but substantially reduces the chance of damage to the balloon wall upon withdrawal through a guide catheter. It increases the ability of the deflated balloon to pass through tight stenoses. The reduced profile of balloon 20 prevents the balloon from being caught at the distal end of a guide catheter and substantially reduces the surface area of the balloon which is in contact with the guide catheter lumen during withdrawal.

FIGS. 5 and 6 show alternate embodiments of the pleated dilatation balloon of FIG. 4. In FIG. 5, a pleated balloon 50 has a collapsed configuration about catheter shaft 52 which is characterized by four pleats 56 disposed intermediate wings 58. The folding of balloon 50 into the illustrated configuration results from four lines of reduced wall thickness formed along the balloon. Similarly, as shown in FIG. 6, a five pleat balloon 60 has a collapsed configuration about catheter shaft 62 which is characterized by five pleats 69 intermediate five wings 68. From a comparison of FIGS. 4, 5 and 6, it can be appreciated that the profile of the pleated balloon decreases as the number of pleats increase. Generally, the larger the diameter of the balloon, the greater the number of pleats which may be formed into the balloon.

A further advantage of the present invention is that the lines extending longitudinally of the balloon may be manufactured to provide a minimum burst strength for the balloon. Presently, if a balloon does not deflate when desired, a practitioner may over inflate the balloon to intentionally rupture the balloon wall, causing immediate deflation of the balloon and enabling withdrawal of the balloon from the lumen. Lines 44 of FIG. 3 may be formed so as to serve as rupture points which would insure that the burst pressure of balloon 20 would not exceed the delivery capability of a selected clinical inflation device. A pleated balloon in accordance with the present invention may have a minimum burst pressure of 16 to 18 Bars compared to the more than 20 Bar minimum burst pressure of some dilatation balloons.

The invention is also useful in balloons where the nature of the material or balloon geometry is such that the balloon is susceptible to damage from handling and use. In some instances, it has been the practice to thicken the wall of such a balloon in order to make it more resistant to damage. An undesired by product of such a thickened balloon wall, however, may be that the burst pressure is increased far beyond that needed for the intended application. With the present invention, such a balloon may have the increased wall thickness while maintaining an acceptable burst pressure.

A method for making a pleated balloon in accordance with the present invention involves extruding a tube of polymeric material, such as polyvinyl chloride, polyethylene, or polyethylene terephthalate so as to have at least three circumferentially spaced elongated segments of less wall thickness than the remainder of the tube. As shown in FIG. 7, a tube 60 is formed of relatively thick wall portions 63, 65 and 67 which are disposed intermediate relatively thin walled portions 62, 64 and 66. In the FIG. 7 embodiment, thin walled portions are defined by chordal flats formed in an angular spacing of 120° circumferentially about the tube. Each of the flats may define a chord corresponding to approximately 10% of the outer circumference of the tube. By way of example, for a polyethylene terephthalate tube intended to be formed into a 3.0 mm diameter balloon, the tube may have an inner diameter of about 0.0169", having thick walled portions of about 0.0050", the thin walled portions of the tube should be about 0.0038". The thin walled portions 62, 64 and 66 are implemented as thin lines which extend longitudinally of the extruded tube 60. A balloon formed from tube 60 preferentially collapses at thin walled portion 62, 64 and 66 while the thick walled portions 63, 65 and 67 project radially outward to form the wings.

Following extrusion of tube 60, the tube is then blow molded in accordance with the techniques disclosed in U.S. Pat. No. 4,490,421, and U.S. patent application Ser. No. 001,759, filed Jan. 9, 1987 now abandoned, the disclosures of which are incorporated herein by reference. Once tube 60 has been extruded, the tube is inserted into a mold chamber. Upon heating the chamber, the tube is heated by convection and radiation thereby softening the tube material. It will be appreciated that certain polymeric materials do not require heating to soften the tube material. Tube 60 is then axially stretched while positive pressure is simultaneously applied to the interior of the tube. The radial expansion, caused by the positive pressure on the tube interior, during axial stretching establishes biaxial stretching of the tube. The biaxial stretching is maintained until the tube assumes the shape of the mold. It should be noted that the cones and neck portions of the balloon also are formed from the tube 60 having alternate thick and thin wall portions. As a result, the cones 24, 26 of the balloon also define a pleated arrangement and will tend to collapse into the pleated configuration when the balloon is aspirated. This may effectively reduce the angle made by the cone and may facilitate entry of the balloon into a tight stenosis. Additionally, by including the pleats in the cone regions, it may be possible to form balloons in which the cone regions fold down closely to the shaft.

From the foregoing, it will be appreciated that the invention provides a dilatation balloon having a tendency to collapse into a pleated configuration forming at least three or more pleats and alternating wings, the radial extension of such wings being relatively small. The pleated balloon folds more easily as it is withdrawn through the guide catheter.

Thus it will be appreciated that the invention provides a new and improved pleated balloon configuration for a dilatation catheter by which the balloon may be more readily contracted to a low profile, as well as a method for forming such a pleated balloon. It should be understood, however, that the foreqoinq description of the invention is intended merely to be illustrative thereof and that other modifications in embodiments may be apparent to those skilled in the art without departing from its spirit. For example, the invention has been illustrated in connection with a coronary dilatation catheter, it may be used with other balloon catheters such as peripheral blood vessel dilatation catheters or esophaqeal catheter. Additionally, although the illustrative embodiment has been described in connection with a balloon made from polyethylene terephthalate, which is relatively inelastic, (non compliant) the invention also may be incorporated in balloons formed from more compliant materials, such as polyvinyl chloride or polyethylene.

Having thus described the invention, what I desire to claim and secure by letters patent is:

1. An angioplasty dilation catheter comprising:
   an elongate flexible shaft having at least one lumen extending therethrough from its proximal to its distal end;
   an imperforate, inelastic angioplasty dilatation balloon mounted on the distal end of the shaft and in fluid communication with the lumen, the balloon being formed from an extruded polymeric tube having at least three circumferentially spaced longitudinally extending extruded fold lines of less wall thickness than the remainder of the tube;
   a fitting for connecting the lumen with an inflation and deflation device; and
   the balloon being adapted for inflation and deflation between an expanded diameter and a collapsed configuration having a reduced cross-sectional profile to facilitate passage of the balloon through a passageway in a body lumen;
   the fold lines being constructed so that when the balloon is caused to collapse, the fold lines will be drawn radially inwardly thereby to define radially inward folds and the portions of the balloon between the fold lines will define radially outward folds.

2. A dilatation catheter as defined in claim 1 wherein the balloon, when deflated, forms at least three pleats about the shaft.

3. A balloon dilatation catheter as defined in claim 1 wherein the balloon is formed from polyethylene terephthalate.

4. A balloon dilatation catheter as defined in claim 1 wherein the balloon is formed from polyethylene.

5. A balloon dilatation catheter as defined in claim 1 wherein the balloon is formed from polyvinyl chloride.

6. A dilatation catheter as defined in claim 1 wherein the catheter comprises a percutaneous transluminal coronary angioplasty catheter.

7. A balloon for an angioplasty dilatation catheter comprising:
   the balloon being formed by radial expansion of an extruded tubular polymeric member having an inperforate wall and having at least three extruded fold lines of reduced wall thickness extending longitudinally of the tube;
   the balloon being formed to collapse under the influence of reduced internal pressure into a configuration defined by at least three longitudinally extending pleats and alternating wings, the extruded fold lines being constructed so that when the balloon is caused to collapse, the fold lines will define radially inwardly disposed folds and the regions between the fold lines will define radially outwardly disposed folds; and
   the wings being flexible and being bendable as to be capable of wrapping about a longitudinally extending dimension of the balloon, thereby to define a smaller cross-sectional profile for the balloon.

8. A method for performing a dilatation procedure in a lumen of a patient comprising:
   inserting a guiding conduit to a region to be dilated;
   providing a dilatation catheter having an imperforate, inelastic angioplasty dilatation balloon formed from an extruded polymeric tube having at least three circumferentially spaced longitudinally extending extruded fold lines of less wall thickness than the remainder of the tube such that said balloon collapses under the influence of negative pressure extending pleats and alternating wings;
   deflating the balloon to the collapsed configuration to cause the fold lines to be drawn radially inwardly thereby to define radially inward folds with the portions of the balloon between the fold lines defining radially outward folds;
   passing the catheter with the collapsed balloon through the guide conduit and out the distal end of the guide conduit;
   inflating the balloon to perform a dilatation and then deflating the balloon to the collapsed configuration; and
   removing the catheter through the guiding conduit while the wings of the balloon ar wrapped about the catheter.

9. A dilatation catheter comprising:
   an elongate flexible shaft having at least one lumen extending therethrough from its proximal to its distal end;
   an imperforate dilatation balloon mounted on the distal end of the shaft and in fluid communication with the lumen, the balloon having at least one segment of a less wall thickness than the remainder of the balloon, the balloon being constructed to be inflated to a pressure sufficient to perform a dilatation, said segment of less wall thickness being defined by a longitudinally extending line along the balloon wall whereby the balloon will burst along said longitudinally extending line; and
   a fitting for connecting the lumen with an inflation and deflation device;
   the wall thickness in the reduced wall thickness providing a weakened area of the balloon adapted to burst when the balloon is subjected to a pressure that exceeds a predetermined maximum pressure no greater than about 18 bars.

10. A dilatation catheter as defined in claim 9 wherein said pressure for performing a dilatation comprises at least about 75 psi.

* * * * *